(12) United States Patent
Letard et al.

(10) Patent No.: US 8,753,743 B2
(45) Date of Patent: Jun. 17, 2014

(54) NANOPARTICLES OF A SPIN TRANSITION COMPOUND

(75) Inventors: Jean-Francois Letard, Canejan (FR); Olivier Nguyen, Hostens (FR); Nathalie Daro, Pessac (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/619,187

(22) Filed: Sep. 14, 2012

(65) Prior Publication Data

US 2013/0011680 A1  Jan. 10, 2013

Related U.S. Application Data

(63) Continuation of application No. 12/096,746, filed as application No. PCT/FR2006/002651 on Dec. 5, 2006, now abandoned.

(30) Foreign Application Priority Data

Dec. 8, 2005  (FR) ..................................... 05 12476

(51) Int. Cl.

| | | |
|---|---|---|
| C07F 15/02 | (2006.01) | |
| C07F 19/00 | (2006.01) | |
| B32B 5/16 | (2006.01) | |
| B32B 9/04 | (2006.01) | |
| B82Y 15/00 | (2011.01) | |
| B82Y 10/00 | (2011.01) | |
| B82Y 20/00 | (2011.01) | |
| B82Y 40/00 | (2011.01) | |

(52) U.S. Cl.

USPC ........... 428/405; 428/913; 428/402; 548/109; 977/773; 977/788; 977/927; 977/943; 977/935; 977/896

(58) Field of Classification Search

None
See application file for complete search history.

(56) References Cited

U.S. PATENT DOCUMENTS

| | | | |
|---|---|---|---|
| 5,582,900 A | 12/1996 | Khan et al. | |
| 5,618,514 A | 4/1997 | Schroder et al. | |
| 5,705,248 A | 1/1998 | Kahn et al. | |
| 5,789,054 A | 8/1998 | Kahn et al. | |
| 6,043,008 A | 3/2000 | Kahn et al. | |
| 6,200,730 B1 | 3/2001 | Khan et al. | |
| 6,255,026 B1 | 7/2001 | Kahn et al. | |
| 6,548,168 B1 | 4/2003 | Mulvaney et al. | |
| 2007/0244265 A1 | 10/2007 | Matyjaszewski et al. | |

FOREIGN PATENT DOCUMENTS

| | | |
|---|---|---|
| EP | 0 666 561 A1 | 8/1995 |
| EP | 0 745 986 A1 | 12/1996 |
| EP | 0 842 988 A1 | 5/1998 |
| EP | 0 543 465 B1 | 7/1999 |

OTHER PUBLICATIONS van Koningsbruggen et al. Non-classical Fe(II) spin-crossover behavior in polymeric iron(II) compounds of formula [Fe(NH2trz)3]X2-xH2O. J. Mater. Chem. 1997, 7, 2069-75.*
Bousseksou et al. "Observation of a thermal hysteresis loop in the dielectric constant of spin crossover complexes: towards molecular memory devices." J. Mater. Chem. 2003, 13, 2069-71.*
Kolnaar et al. "Synthesis, Structure and Properties of a Mixed Mononuclear/Dinuclear Iron(II) Spin-Crossover Compound with the Ligand 4-(p-Tolyl)-1,2,4-triazole." Eur. J. Inorg. 1999, 5, 881-6.*
Varnek et al. "Mossbauer Studies of Fe.x.Zn.1-x(4-Amino-1,2,4-Triazole) 3(NO3)2 Complexes Possessing the 1A1-5T2 Spin Transition." J. Struct. Chem. 1994, 35, 842-50.*
Vaucher, S. et al., "Synthesis of Prussian Blue Nanoparticles and Nanocrystal Superlattices in Reverse Microemulsions" *Angew. Chem. Int. Ed.* 39.10 (2000):1793-1796.
Kume, S. et al., "Photoresponsive molecular wires of FeII triazole complexes in organic media and lightinduced morphological transformations" *Chem. Commun.* 23 (2006):2442-2444.

* cited by examiner

*Primary Examiner* — Samantha Shterengarts
*Assistant Examiner* — Amanda L Aguirre
(74) *Attorney, Agent, or Firm* — Merchant & Gould

(57) ABSTRACT

The invention relates to a material composed of nanoparticles essentially comprising a spin transition compound. The compound corresponds to the formula

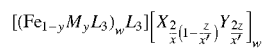

in which L represents a 1,2,4-triazole ligand carrying an R substituent on the nitrogen in the 4 position; X is an anion having the valency x, $1 \leq x \leq 2$; Y is an anion other than X having the valency x', $1 \leq x' \leq 2$; R is an alkyl group or an $R^1R^2N$— group in which $R^1$ and $R^2$ represent, each independently of the other, H or an alkyl radical; M is a metal having a $3d^4$, $3d^5$, $3d^6$ or $3d^7$ configuration, other than Fe; $0 \leq y \leq 1$; $0 \leq z \leq 2$; $3 \leq w \leq 1500$. Applications: thermochromic pigment, data storage, optical limiters, contrast agent.

18 Claims, 6 Drawing Sheets

~ 1 nm

~ 2 nm

~ 3 nm

NANOPARTICLES OF A SPIN TRANSITION COMPOUND

CROSS-REFERENCE TO RELATED APPLICATION

This application is a continuation of U.S. patent application Ser. No. 12/096,746, filed Jun. 9, 2008, which is a National Stage Entry of PCT/FR06/02651, filed Dec. 5, 2006, which in turn claims priority from French Application No. 0512476, filed Dec. 8, 2005. The contents of these applications are incorporated herein by reference in their entirety.

FIELD OF THE INVENTION

The present invention relates to a material composed of particles having nanometric dimensions essentially comprising a spin transition compound, to a process for the preparation of said material and to various applications of the material.

BACKGROUND OF THE INVENTION

It is known to use compounds which exhibit a spin transition for various applications, in particular for information storage. Such compounds can in particular be coordination complexes comprising one or more metal centers having a $3d^4$, $3d^6$ or $3d^7$ configuration, one or more nitrogenous ligands and one or more anions, such as described, for example, in EP-0 543 465, EP-0 666 561, EP-0 745 986 and EP-0 842 988.

EP-0 543 465 describes a process for the preparation of spin transition compounds and the use for information storage. The process consists in bringing together, on the one hand, the ligand and, on the other hand, an iron salt in an acid solution, in allowing to react, in order to obtain a precipitate, and in recovering the precipitate in the powder form. For the use for data storage, the complex obtained is reduced beforehand to a powder in order to be deposited on a support by various methods. The compounds mentioned correspond to one of the following formulae:

FeL$_3$(NO$_3$)$_2$ in which L is a ligand of the 1,2,4-triazole or 4-amino-1,2,4-triazole type, in combination with the NO$_3^-$ anion;

Fe(ATP)$_{2.5}$Cl$_2$, in which the ATP ligand is 4-amino-1,2,4-triazole in combination with Fe(II) and with Cl$^-$;

Fe(TP)$_2$Cl$_2$ in which the TP ligand is 1,2,4-triazole, in combination with Cl$^-$;

[Fe(2-aminomethylpyridine)$_3$]Cl$_2$EtOH, EtOH being ethanol;

[Fe(1,10-phenanthroline)$_2$](NCS)$_2$;

[Fe(1-propyltetrazole) 6](BF$_4$)$_2$;

complexes of a metal M in combination with a mixture of several ligands (chosen from R-Trz, amines NL$_2$ and triazolates Trz-, M being Fe(II), Fe(III) or Co(II), R-Trz being a triazole carrying an R substituent, R and L being an alkyl or H) and with an anion chosen from BF$_4^-$, ClO$_4^-$, CO$_3^{2-}$, Br$^-$ and Cl$^-$, the complex additionally comprising a defined amount of water.

With the exception of [Fe(1,10-phenanthroline)$_2$(NCS)$_2$], all these complexes are pink in color in the low spin (LS) state and white in the high spin (HS) state. The transition is brought about by heating or cooling and takes place between −20° C. and 100° C. They exhibit a phenomenon of hysteresis which can range from a few degrees to a few tens of degrees.

EP-0 666 561 describes spin transition compounds which correspond to the formula Fe(II)(H-Trz)$_3$(X)$_2$ in which Trz is 1,2,4-triazole and (X)$_2$ represents the anion (BF$_4^-$)$_2$, (ClO$_4^-$)$_2$, (Br$^-$)$_2$, (Cl$^-$)$_2$ or (CO$_3^{2-}$). These compounds exhibit two crystalline phases, each having spin transitions associated with a change in color (white/pink) and for which the temperatures T$_{1/2}$↓ and T$_{1/2}$↑ are respectively less than and greater than ambient temperature. The preparation process is analogous to that described in EP-0 543 465 above.

EP-0 745 986 describes compounds corresponding to a formula analogous to that of the compounds of EP-0 543 465, in which M is a metal ion of $d^5$, $d^6$ or $d^7$ configuration, the ligand is a dialkylaminotriazole and the anion comprises a sulfitoaryl, sulfitoalkyl, sulfitoaryl halide or sulfitoalkyl halide group. These specific compounds have a hysteresis amplitude of greater than 70° C. and a region of bistability centered exactly around ambient temperature. Said compounds are pink in the LS state and white in the HS state. The process for the preparation of the compounds, described very briefly, is analogous to that described in EP-0 543 465 above.

EP-0 842 988 describes spin transition chemical compounds and their use in display devices where a temperature threshold is exceeded. The compounds are formed by a network composed of molecules each formed by a metal-ligand complex and by an anion, and they comprise at least one water molecule bonded to the ligand via a hydrogen bond. The metal is chosen from those which have a $d^4$, $d^5$, $d^6$ or $d^7$ configuration. The ligand is 1,2,4-triazole carrying an R substituent comprising an OH group. The anions are nitrate and tosylate derivatives. The compounds corresponding to this definition have a temperature T$_{1/2}$↑ of between 80 and 95° C. and a T$_{1/2}$↓ of −170° C. They can be used in particular in devices intended to detect an accidentally high (of the order of 80° C.) storage temperature in storage buildings or transportation vehicles. The compounds are prepared by mixing a precursor of the metal center and a precursor of the ligand, at ambient temperature, and by removing the solvent by filtration after a precipitate has been obtained. The compound is obtained in the pulverulent form.

The compounds obtained according to the prior art above are of micrometric size and have to be ground in order to be usable as thermochromic pigments in polymer films having a micrometric thickness or as data carrier in Microsystems, the carriers having to remain transparent.

SUMMARY OF THE INVENTION

The aim of the present invention is to provide a process for the direct production of nanoparticles formed of complexes of iron, of a triazole ligand and of at least one anion.

The subject matter of the present invention is consequently a material in the form of nanoparticles formed of complexes, a process for the production of said material and applications of said material.

The material according to the present invention is composed of nanometric particles essentially comprising a compound corresponding to the formula:

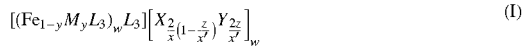

in which:

L represents a 1,2,4-triazole ligand carrying an R substituent on the nitrogen in the 4 position;

X is an anion having the valency x, 1≤x≤2;

Y is an anion other than X having the valency x', 1≤x'≤2;

R is an alkyl group or an $R^1R^2N-$ group in which $R^1$ and $R^2$ represent, each independently of the other, H or an alkyl radical;

M is a metal having a $3d^4$, $3d^5$, $3d^6$ or $3d^2$ configuration, other than Fe;

$0 \leq y \leq 1$;
$0 \leq z \leq 2$;
$3 \leq w \leq 1500$.

In the continuation of the text, the ligand "1,2,4-triazole carrying an R substituent on the nitrogen in the 4 position" is denoted without distinction by L or by R-Trz.

The term "nanometric" particles is understood to mean particles which have a mean diameter between 1 nm and 500 nm, more particularly between 1 and 100 nm. When w is respectively 3, 300 or 1500, the mean size of the particles is respectively approximately 1 nm, 100 nm or 500 nm.

A compound which corresponds to the above definition is capable of reversibly changing spin state when heated or when cooled, with a changing color associated with each change in spin.

When an R substituent is an alkyl group, it is preferably chosen from alkyl groups having from 1 to 8 carbon atoms, more particularly from 1 to 4 carbon atoms. When an R substituent is an $R^1R^2N-$ group, $R^1$ and $R^2$ represent, independently of one another, preferably H or an alkyl group having from 1 to 8 carbon atoms, more particularly from 1 to 4 carbon atoms.

Each of the anions X and Y can be a monovalent anion or a divalent anion. The monovalent anion is chosen from $BF_4^-$, $ClO_4^-$, $Br^-$, $Cl^-$ and $NO_3^-$. The divalent anion is preferably chosen from $SO_4^{2-}$ and $CO_3^{2-}$. The choice of the anions makes it possible to control the spin transition (in particular the abrupt nature, the presence of hysteresis and the position of the transition).

Figure 1:
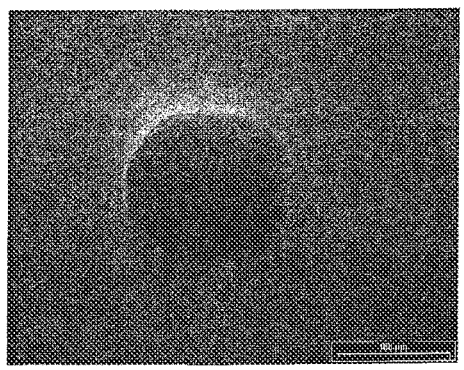
FIGS. 1 and 2 are TEM images of the $[Fe(NH_2Trz)_3](Br)_2$ complex nanoparticles of Example 1 a very uniform structuring of the nanoparticles in the spherical form.

This silica shell, with a size of a few nanometers, is reflected by a diffuse coating around the particle.

DETAILED DESCRIPTION OF THE PREFERRED EMBODIMENTS

In a specific embodiment, y=0 and z=0, and the material constituting the nanoparticles corresponds to the formula $[(FeL_3)_w L_3][X_{2/x}]_w$.

In another embodiment, y.noteq.0 and z=0. M then acts as doping agent for the spin transition phenomenon of the compound $[(Fe_{1-y}M_y L_3)_w L_3][X_{2/x}]_w$. An increase in y reduces the abrupt nature of the transition and the intensity of the pink color corresponding to the low spin state. Mention may be made, as an example of metal M, of the zinc(II), manganese (II) nickel(II), and cobalt(II) ions.

In a specific embodiment, $z \neq 0$. The choice of the anions X and Y makes it possible to adjust the spin transition temperature and to vary the abrupt nature of the spin transition. Mention may be made, as an example of mixture of anions, of the $BF_4$ and $NO_3$ pair, the Br and $NO_3$ pair, or the Cl and $NO_3$ pair.

In another embodiment, the complex nanoparticles are coated with a silica film.

The characteristics indicated for the various embodiments can, of course, exist alone in a material or in the form of a combination of at least two of them.

The material proposed is obtained from a solution of Fe(II) salt and optionally of a precursor of the metal M in a solvent or a mixture of solvents and from a solution of ligand R-Trz in a solvent or a mixture of solvents.

In a first embodiment, the preparation is carried out by a reverse micelle synthesis. The process comprises the following stages:

a) preparation of an emulsion of the water-in-oil type by addition, with vigorous stirring, of a composition of oil possessing surfactant properties type to an aqueous solution of at least one iron salt comprising ascorbic acid;

b) preparation of an emulsion of the water-in-oil type by addition, with vigorous stirring, of a composition of oil possessing surfactant properties type to an aqueous solution of a ligand;

c) mixing the two emulsions, followed by further vigorous stirring, for a time of 1 to 10 min;

d) precipitation of the nanoparticles by addition of a solvent which does not modify the structure of the nanoparticles and which denatures the emulsion, for example ethyl ether;

e) extraction of the precipitate by several "washing with said solvent/centrifuging" cycles, followed by evaporation of said solvent.

The composition of the oil possessing surfactant properties type can be either a composition obtained by addition of a surfactant to an oil or a single product having both surfactant properties and oil properties (such as the products sold under the names LAUROPAL®, TERGITOL® or IFRALAN®).

The size of the particles formed can be controlled in particular by the choice of the reaction temperature and/or of the duration of contacting of the two microemulsions prepared respectively during stages a) and b). All things otherwise being equal, an increase in the duration and/or in the temperature promotes an increase in the size of the final particles.

In another embodiment, the preparation is carried out by a microemulsion synthesis. The process comprises the following stages:

a) preparation of a microemulsion of the water-in-oil type by addition of an aqueous solution of at least one iron salt to a solution of a surfactant in an oil (n-heptane, for example) and subjecting to ultrasound until a clear solution is obtained;
b) preparation of a microemulsion of the water-in-oil type by addition of an aqueous solution of ligand to a solution of a surfactant in an oil and subjecting to ultrasound until a clear solution is obtained;
c) mixing the two microemulsions and treating the mixture with ultrasound until a clear solution is obtained;
d) precipitation of the nanoparticles by addition of a solvent which does not modify the structure of the nanoparticles but which denatures the emulsion, for example ethanol.

The proportions of solvent, of surfactant and of oil which are required in order to obtain a microemulsion are determined from the phase diagram of the ternary mixture. The ternary phase diagram is available in the literature for numerous solvent/oil/surfactant combinations. The determination of a specific ternary diagram is within the scope of a person skilled in the art.

In the two embodiments of the preparation of the materials of the invention:
when y≠0 and z=0, an aqueous solution of M salt is prepared and added to the aqueous solution of Fe salt, before bringing into contact with the "surfactant+oil" mixture;
when z≠0 and y=0, an aqueous solution comprising an Fe salt of one of the anions and an Fe salt of the other anion is prepared, before bringing into contact with the "surfactant+oil" mixture;
when y≠0 and z.noteq.0, a solution comprising at least one iron salt of one of the anions and at least one M salt of the other anion is prepared.

In the two embodiments of the process for the preparation of the materials of the invention, when the desired material is composed of nanoparticles coated with silica, a silyl derivative is added to the reaction medium, before denaturation of the micelle or of the microemulsion (that is to say, before stage d) in the two embodiments described above). Mention may be made, as example of silyl derivative, of tetraethoxysilane, (n-octadecyl)triethoxysilane and (n-octyl)triethoxysilane.

The material in the form of nanoparticles of the present invention is of particular use as thermochromic pigment. By way of example, in the field of plastics technology, the application of a varnish is often carried out in the form of a layer with a thickness of a few microns. The nanoparticles proposed can be incorporated directly into a polymer matrix which will be applied to a substrate in the form of a layer with a thickness of the order of a micrometer, whereas, in the prior art, a preliminary stage in which microparticles of spin transition material are ground is necessary.

The material in the form of nanoparticles according to the invention is in addition of use for data storage. The nanoparticles constitute a true "molecular memory" using the phenomenon of spin transition. A bit of information can thus be stored in each nanoparticle. The perfect transparency of a disk composed of a polymer matrix built with these bistable nanoparticles makes it possible to envisage applications in the field of bulk data storage (holography).

The significant modification in color (that is to say of the absorption spectrum) associated with the phenomenon of spin transition is reflected by a change in the refractive index of the material between the low spin state and the high spin state. The respective refractive indices of the two states can be adjusted in order to render the medium transparent when the molecules are in the HS state. At high optical energy, the photo-induced effects can bring about switching from the HS state to the LS state and can thus bring about a variation in the refractive index. The initially transparent medium then becomes opaque. This phenomenon makes possible the use of the nanoparticles in the field of optical limiters and also as optical gate for data storage.

Nanoparticles of a material having a magnetic response which changes with temperature from a diamagnetic form (LS state) to a paramagnetic form (HS state) can be used for the preparation of heat-sensitive contrast agents for thermotherapy methods. The nanoparticles, positioned in situ, would make it possible to monitor the crossing of a temperature threshold, such as that which distinguishes healthy cells from cancer cells. This is because the magnetic resonance image (MRI) of a medium comprising the nanoparticles is normal in the case of the nanoparticles in the diamagnetic low spin state and highly distorted in the case of a paramagnetic high spin state.

The present invention is described in more detail with the help of the following examples, which are given by way of illustration and to which the invention is, of course, not limited.

EXAMPLE 1

A material was prepared by an inverse emulsion synthesis according to the following procedure.

The addition is carried out, to a round-bottomed flask A comprising $m_1$ g of an iron(II) salt and $m_2$ g of ascorbic acid, of $m_3$ g of water.

The addition is carried out, to a round-bottomed flask B comprising $m_4$ g of 4-amino-1,2,4-triazole ($NH_2Trz$), of $m_3$ g of water.

The compounds are dissolved in the two round-bottomed flasks by mechanical stirring in a water bath at 50° C. Subsequently, $m_5$ g of surfactant (LAUROPAL® 205 or IFRALAN® D205 or TERGITOL®, which act both as surfactant and as oily phase) are added.

The round-bottomed flasks A and B are subsequently subjected to mixing using a vortex mixer, which generates vigorous mechanical stirring favorable for the formation of micelles. The two reverse micelles thus obtained are thermodynamically stable for several minutes. The contents of the round-bottomed flask B are rapidly added to the contents of the round-bottomed flask A and then the combined mixture is subjected to mixing using a vortex mixer for several minutes in order to promote micelle exchange.

The particles are finally obtained by addition of diethyl ether, which has the effect of denaturing the reverse micelle. The diethyl ether dissolves the surfactant and not the complex formed. After centrifuging and removing the liquid phase, the washing operation is repeated an additional 3 to 4 times until the supernatant liquid is perfectly clear.

The specific conditions under which several samples were prepared are summarized in table 1.

TABLE 1

| | Round-bottomed flask A | | | | Round-bottomed flask B | | |
|---|---|---|---|---|---|---|---|
| Sample 1 | Fe(II) salt $m_1$ | Water $m_3$ | Ascorbic acid $m_2$ | Surfactant $m_5$ | Ligand $m_4$ | Water $m_3$ | Surfactant $m_5$ |
| 2 | FeBr$_2$ 0.23 g | 0.8 g | 0.03 g | Ifralan 4.2 g | NH$_2$Trz 0.27 g | 0.8 g | Ifralan 4.2 g |
| 3 | FeCl$_2$ 0.21 g | 0.8 g | 0.03 g | Ifralan 4.2 g | NH$_2$Trz 0.27 g | 0.8 g | Ifralan 4.2 g |
| 4 | Fe(BF$_4$)$_2$ 0.36 g | 0.8 g | 0.03 g | Ifralan 4.5 g | NH$_2$Trz 0.27 g | 0.8 g | Ifralan 4.5 g |
| 5 | Fe(NO$_3$)$_2$ 2.3 ml | | 0.03 g | Ifralan 8.9 g | NH$_2$Trz 0.27 g | 2.3 g | Ifralan 8.9 g |

\*\*Fe(NO$_3$)$_2$, (salt not commercially available) is obtained in solution in water by mixing an aqueous FeSO$_4$ solution (1.485 g in 2.5 ml) comprising ascorbic acid with an aqueous Ba(NO$_3$)$_2$ solution (1.4 g in 7 ml), followed by removal of the BaSO$_4$ precipitate by filtration. A volume of this solution is withdrawn in order to prepare the Fe(NH$_2$Trz)$_3$(NO$_3$)$_2$ nanoparticles.

Figure 2:
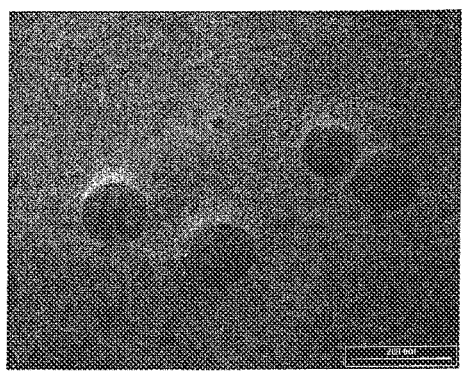
Figure 3:
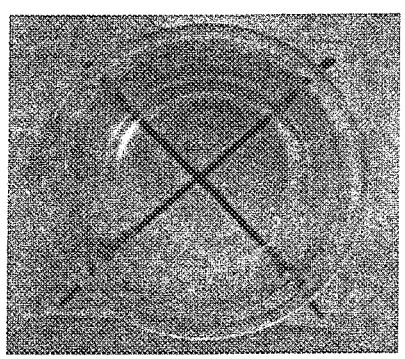
FIG. 3 is a TEM image of a polymer doped with nanometric particles of Example 1 demonstrating the transparency.

TEM images of the [Fe(NH$_2$Trz)$_3$](Br)$_2$ complex nanoparticles obtained in tests No. 1 are represented in FIGS. 1, 2 and 3. The images of FIGS. 1 and 2 show a very uniform structuring of the nanoparticles in the spherical form. This structure results from the fact that the synthetic reaction is confined to nanodroplets. The size of the particles is of the order of 100 nm, which typically corresponds to a value of 300 for w in the formula (I). The transparency of a polymer doped with nanometric particles is demonstrated in FIG. 3.

Figure 4:
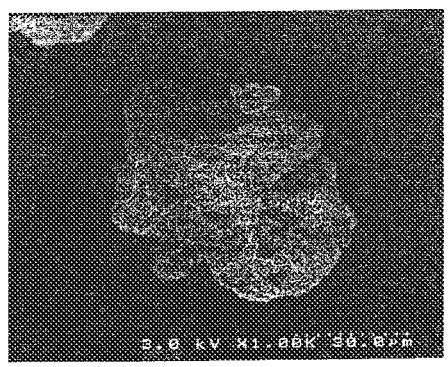
FIGS. 4 and 5 show that the spin transition particles synthesized by the process of the prior art do not have uniform structuring.
Figure 5:
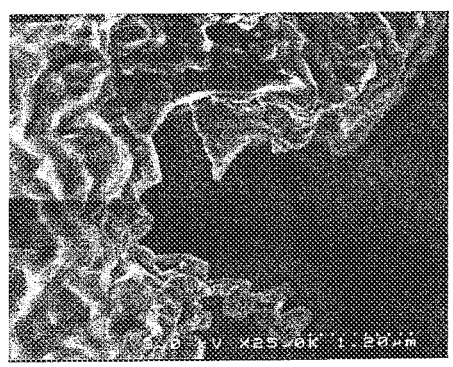
Figure 6:
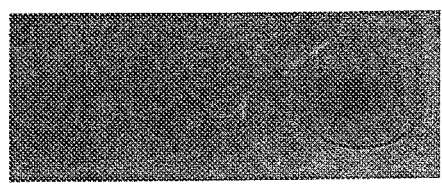
FIG. 6 shows the opaqueness generated by the introduction of micrometric particles of the prior art (even in small proportions) into a structuring polymer (of PVA type) which is originally transparent.

By way of comparison, a complex was prepared according to the process of the prior art, starting from the same precursors. The precursors were mixed at ambient temperature and a precipitate formed was separated by filtration. TEM images of the precipitate obtained are represented in FIGS. 4, 5 and 6. FIGS. 4 and 5 show that the spin transition particles synthesized by the process of the prior art do not have uniform structuring. The grains are nonuniform and have a size of the order of 60 .mu.m. The opaqueness generated by the introduction of micrometric particles (even in small proportions) into a structuring polymer (of PVA type) which is originally transparent is shown in FIG. 6.

EXAMPLE 2

A material was prepared by a microemulsion synthesis under the following conditions.

0.648 ml of a 0.5M solution of FeBr$_2$ in water was prepared and then this solution was added to a solution of 1.6 g of sodium bis(2-ethylhexyl)sulfosuccinate (AOT) in 46 ml of n-heptane. The mixture thus obtained was subjected to ultrasound until a clear solution was obtained.

0.648 ml of a 1.5 M solution of NH$_2$Trz in water was prepared and then this solution was added to a solution of 1.6 g of AOT in 46 ml of n-heptane. The mixture thus obtained was subjected to ultrasound until a clear solution was obtained.

The two clear solutions were subsequently mixed and this new mixture was subjected to ultrasound until a clear final solution was obtained. Analyses by light scattering showed particles of the order of 3 nm, which typically corresponds to a value of 9 for w in the formula (I). The clear solution is pink in the low spin state and white in the high spin state. This reversible modification in the color from pink to white by a change in the temperature demonstrates that the spin transition phenomenon occurs on the scale of the nanomaterial in situ.

The particles are finally obtained by addition of ethanol, the effect of which is to denature the inverse microemulsion. The ethanol dissolves the surfactant and not the complex formed. After centrifuging and removing the liquid phase, the washing operation is repeated 3 to 4 times until the supernatant liquid is perfectly clear.

EXAMPLE 3

Nanoparticles were prepared starting from an Fe precursor and an M precursor by an inverse emulsion synthesis under the conditions of test No. 3 given in Table 1, 0.116 g of FeCl$_2$ and 0.124 g of ZnCl$_2$, in place of 0.21 g of FeCl$_2$, being introduced into the round-bottomed flask A. Nanoparticles formed by the Fe$_{0.5}$Zn$_{0.5}$Cl$_2$ complex were obtained. The size of the particles is of the order of 100 nm, i.e. typically a w of 300.

EXAMPLE 4

The procedure of example 2 was repeated, the FeBr$_2$ solution being replaced with an FeCl$_2$ and ZnCl$_2$ solution. Nanoparticles formed by the Fe$_{0.5}$Zn$_{0.5}$Cl$_2$ complex were obtained. The size of the particles is of the order of 100 nm, i.e. typically a w of 300.

EXAMPLE 5

The procedure of example 1 was repeated under the following conditions, Fe(BF$_4$)$_2$ being dissolved in the Fe(NO$_3$)$_2$ solution.

TABLE 1

| Round-bottomed flask A | | | | Round-bottomed flask B | | |
|---|---|---|---|---|---|---|
| Fe(II) salt $m_1$ | Water $m_3$ | Ascorbic acid $m_2$ | Surfactant $m_5$ | Ligand $m_4$ | Water $m_3$ | Surfactant $m_5$ |
| Fe(NO$_3$)$_{1.7}$(BF$_4$)$_{0.3}$ Fe(NO$_3$) 1.96 ml Fe(BF$_4$)$_2$ 0.054 g | | 0.03 g | Ifralan 8.5 g | NH$_2$Trz 0.27 g | 1.96 g | Ifralan 8.5 g |

Nanoparticles of an Fe(NH$_2$TrZ)$_3$(NO$_3$)$_{1.7}$(BF$_4$)$_{0.3}$] complex were obtained. The size of the particles is of the order of 100 nm, i.e. typically a w of 300.

Figure 7:
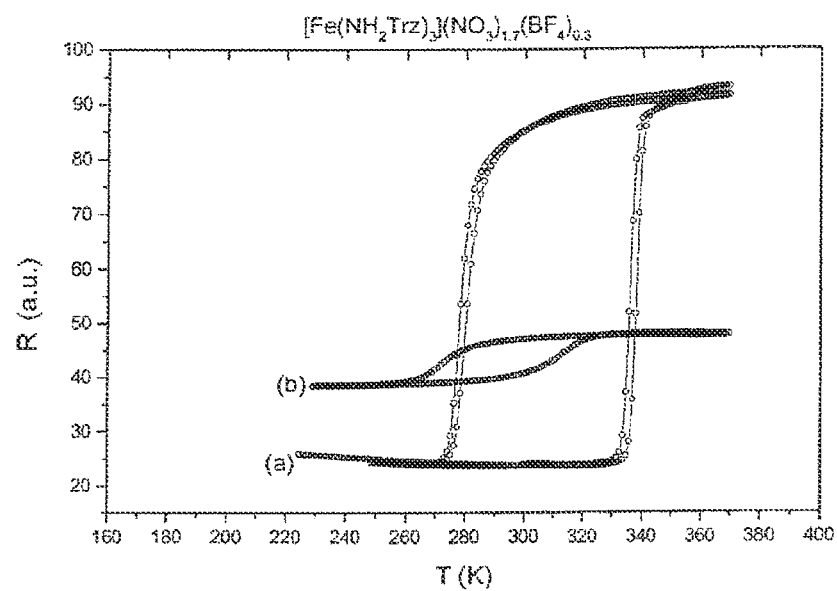
FIG. 7 shows the change in the signal for reflectivity R as a function of the temperature T for the complex of Example 5 (curve b) and for the material with the same formula obtained by conventional synthesis (curve a).

The change in the signal for reflectivity R as a function of the temperature T for the complex of the present example (curve b) and for the material with the same formula obtained by conventional synthesis (curve a) is shown in FIG. 7.

EXAMPLE 6

A material was prepared with a silica coating by a reverse micelle synthesis according to the procedure of example 1 carried out with the precursor FeBr$_2$. The difference from example 1 lies in the fact that, after having mixed the two micelle solutions and stirred using a vortex mixer for a few minutes, 2 ml of tetraethoxysilane (TEOS) were added.

Figure 8:
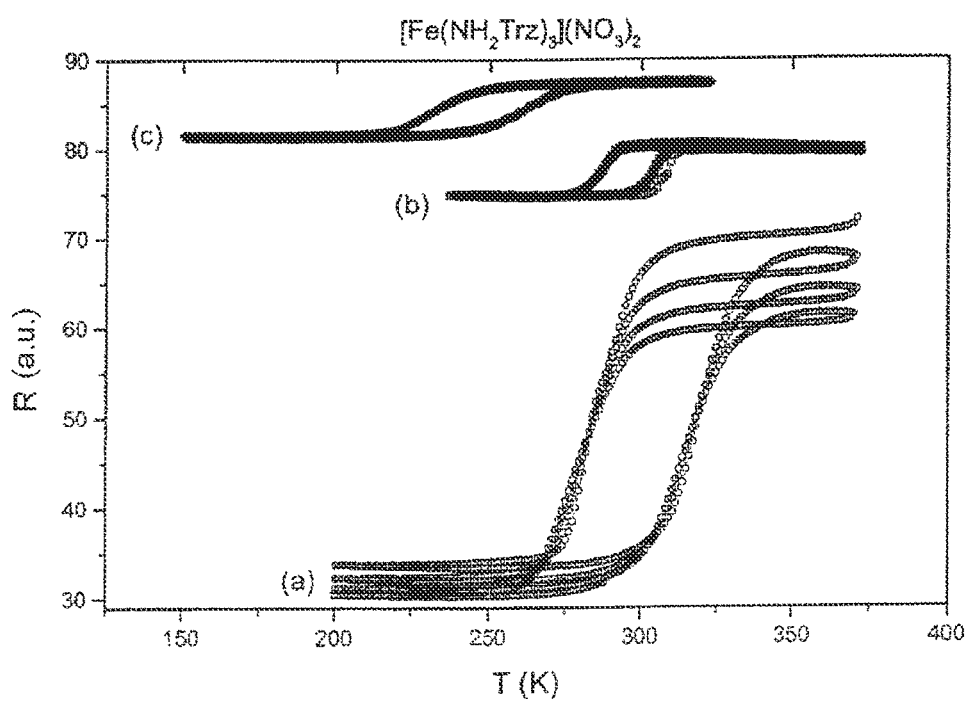
FIG. 8 shows the change in the reflectivity R as a function of the temperature T for the derivative $Fe(NH_2Trz)_3(NO_3)_2$ synthesized by the conventional route (a), by the reverse micelle route (b) (test No. 2 in table 1) and by the reverse micelle route with silica coating (c).
Figure 9:
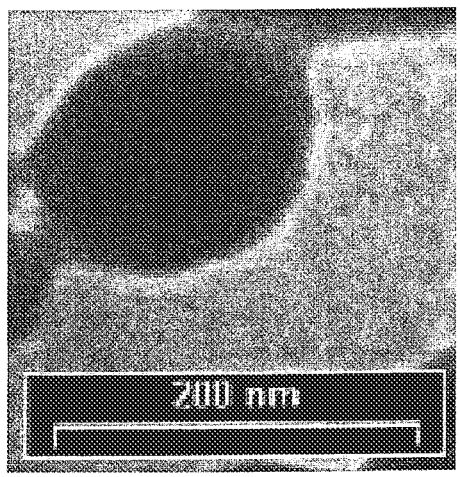
FIG. 9 is a TEM image of a silica coating around a spin transition nanoparticle.

The change in the reflectivity R as a function of the temperature T for the derivative Fe(NH$_2$Trz)$_3$(NO$_3$)$_2$ synthesized by the conventional route (a), by the reverse micelle route (b) (test No. 2 in table 1) and by the reverse micelle route with silica coating (c) is shown in FIG. 8. The TEM image of a silica coating around a spin transition nanoparticle is represented in FIG. 9. This silica shell, with a size of a few nanometers, is reflected by a diffuse coating around the particle.

EXAMPLE 7

A solution of m$_1$ g of FeBr$_2$ in 0.342 g of water and a solution of 0.8 g of AOT in 23 ml of n-heptane were prepared, then the two solutions were mixed and the mixture thus obtained was subjected to ultrasound until a clear solution was obtained, this solution being referred to as solution A.

A solution of m$_2$ g of NH$_2$Trz in 0.342 g of water and a solution of 0.8 g of AOT in 23 ml of n-heptane were prepared, then the two solutions were mixed and the mixture thus obtained was subjected to ultrasound until a clear solution was obtained, this solution being referred to as solution B.

Solutions A and B were subsequently mixed and this new mixture was subjected to ultrasound until a clear final solution was obtained. The particles were obtained according to the procedure of example 2, by addition of and washing with ethanol.

The respective amounts m$_1$ and m$_2$ used for the samples are given in the table below.

| Sample | m$_1$ | m$_2$ |
|---|---|---|
| 7(1) | 0.035 | 0.054 |
| 7(2) | 0.058 | 0.081 |
| 7(3) | 0.081 | 0.108 |

Figure 10A:
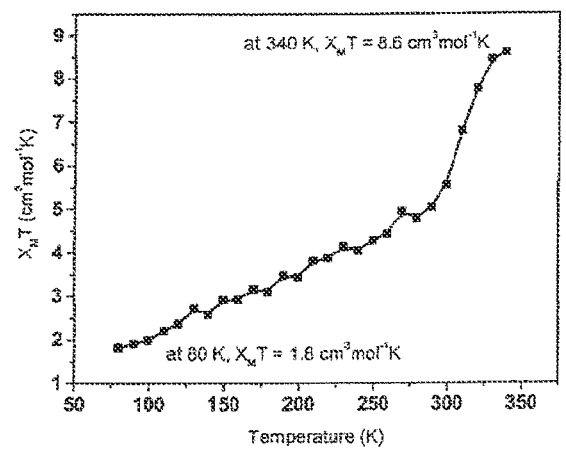
FIGS. 10a, 10b, and 10c show the change in the magnetic signal, expressed as product $\chi_M T$, respectively for samples 7(1), 7(2) and 7(3) of Example 7. The molar magnetic susceptibility $\chi_M$, in $cm^3 mol^{-1}$, multiplied by the temperature T in degrees K, is given on the ordinate and the temperature T in degrees K is given on the abscissa, for the materials for which w=3, 5 and 7.
Figure 10B:
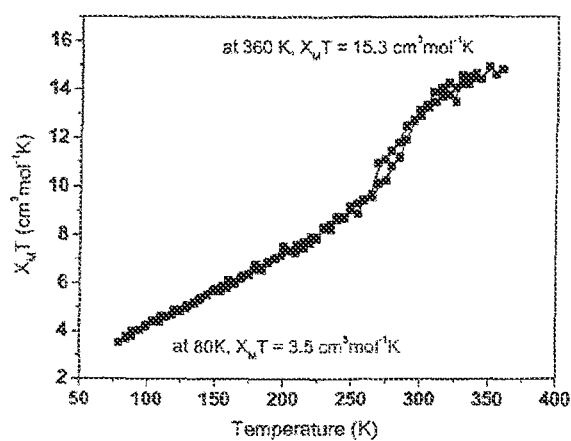
Figure 10C:
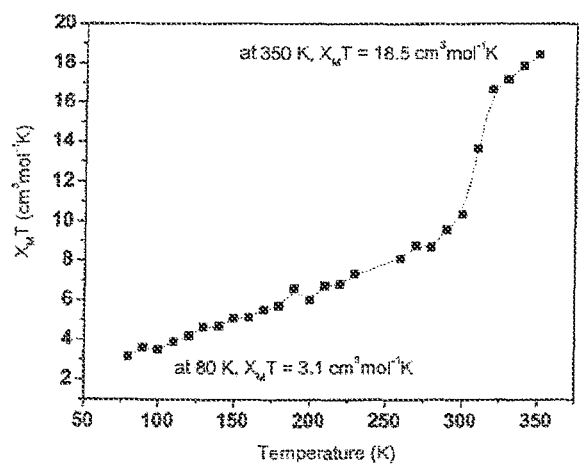
Figure 11A:
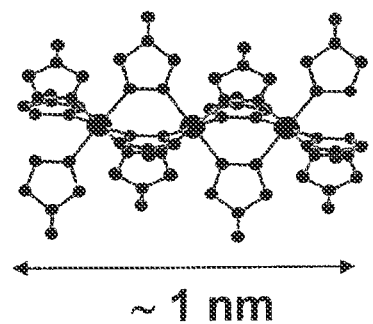
FIGS. 11a, 11b, and 11c illustrates the expanded formula of each of the materials constituting the samples 7(1), 7(2) and 7(3) of Example 7.

The change in the magnetic signal, expressed as product $\chi_M$T, respectively for samples 7(1), 7(2) and 7(3) is shown in FIGS. 10a, b and c. The molar magnetic susceptibility $\chi_M$, in cm$^3$mol$^{-1}$, multiplied by the temperature T in degrees K, is given on the ordinate and the temperature T in degrees K is given on the abscissa, for the materials for which w=3, 5 and 7. The curves confirm the presence of a gradual spin transition for the three nanomaterials about 300 K. They also show that the magnetic value at 350 K is in accordance with the product $\chi_M$T expected for a complex comprising, in the HS state, respectively 3 Fe(II) atoms (W=3) for the sample 7(1), 5 Fe(II) atoms (w=5) for the sample 7(2) and 7 Fe(II) atoms (w=7) for the sample 7(3), thus confirming the formula of the complex. If the distance of the bonds involved in these complexes is taken into account, the size of the nanoparticles w=3 is 1 nm, w=5 is 2 nm and w=7 is 3 nm. The expanded formulae for the samples 7(1), 7(2) and 7(3) respectively are represented in FIGS. 11a, b and c.

The materials obtained correspond to the formula (I) in which y=0, x=1, z=0 and L is NH$_2$Trz, that is to say to the formula

[(FeL$_3$)$_w$L$_3$][X$_2$]$_w$

The size of the particles φ(in nm), the corresponding value of w and the theoretical magnetic value at 350 K $\chi_M$T (in cm$^3$mol$^{-1}$K) are given in the following table.

| Sample | φ | w | $\chi_M$T |
|---|---|---|---|
| 7(1) | 1 | 3 | 9 |
| 7(2) | 2 | 5 | 15 |
| 7(3) | 3 | 8 | 21 |

Figure 11B:
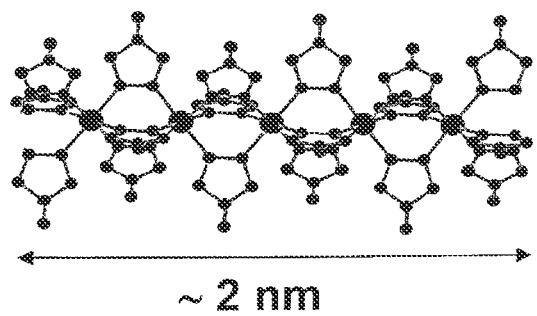
Figure 11C:
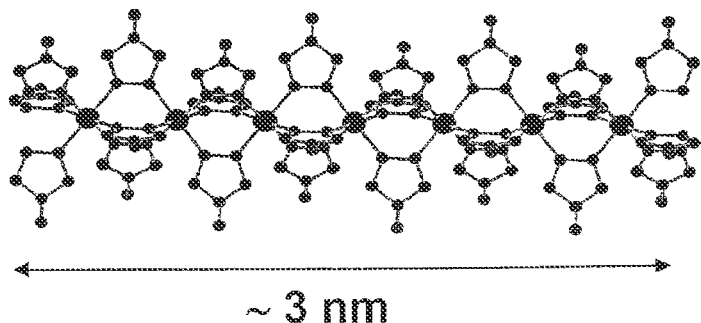

The expanded formula of each of the materials constituting the samples 7(1), 7(2) and 7(3) is represented in FIG. 11.

That which is claimed is:
1. A process for the direct preparation of a spin transition material composed of spherical nanometric particles comprising a compound corresponding to the formula:

$$[(Fe_{1-y}M_yL_3)_wL_3]\left[X_{\frac{2}{x}(1-\frac{z}{x'})}Y_{\frac{2z}{x'}}\right]_w$$

in which:
L represents a 1,2,4-triazole ligand carrying an R substituent on the nitrogen in the 4 position;
X is an anion having the valency x, 1≤x≤2;
Y is an anion other than X having the valency x', 1≤x'≤2;
R is an alkyl group or an R$^1$R$^2$N— group in which R$^1$ and R$^2$ represent, each independently of the other, H or an alkyl radical;
M is a metal having a 3d$^4$, 3d$^5$, 3d$^6$ or 3d$^7$ configuration, other than Fe;
0≤y≤1;
0≤z≤2;
3≤w≤1500;
the process
comprising the following steps:
a) preparation of an emulsion of a water-in-oil type by addition, with vigorous stirring, of a composition of oil possessing surfactant properties to an aqueous solution of at least one iron salt and optionally a precursor of the metal M and comprising ascorbic acid;
b) preparation of an emulsion of a water-in-oil type by addition, with vigorous stirring, of a composition of oil possessing surfactant properties to an aqueous solution of a ligand;
c) mixing the two emulsions, followed by further vigorous stirring, for a time of 1 to 10 min;
d) precipitation of the nanoparticles by addition of a solvent which does not modify the structure of the nanoparticles but which denatures the emulsion; and
e) extraction of the precipitate by several washing with the solvent and centrifuging cycles followed by evaporation of the solvent,
wherein the process does not comprise grounding of the spherical nanometric particles.

2. The process as claimed in claim 1, wherein R is an alkyl group having from 1 to 8 carbon atoms, or R is an $R^1R^2N$— group in which $R^1$ and $R^2$ represent, independently, H or an alkyl group having from 1 to 8 carbon atoms.

3. The process as claimed in claim 1, wherein each of the anions X and Y represents, independently, a monovalent anion selected from the group consisting of $BF_4^-$, $ClO_4^-$, $Br^-$, $Cl^-$ and $NO_3^-$ or a divalent anion selected from the group consisting of $SO_4^{2-}$ and $CO_3^{2-}$.

4. The process as claimed in claim 1, wherein M represents Zn, Mn, Ni or Co.

5. The process as claimed in claim 1, wherein the composition of the oil possessing surfactant properties is a composition obtained by addition of a surfactant to an oil or is a single product having both surfactant properties and oil properties.

6. The process as claimed in claim 1, wherein a material composed of nanoparticles of a compound

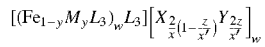

in which y≠0 and z=0 is prepared comprising preparing an aqueous solution of M salt and adding to the aqueous solution of Fe salt, before bringing into contact with the composition of oil possessing surfactant properties.

7. The process as claimed in claim 1, wherein a material composed of nanoparticles of a compound

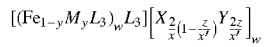

in which z≠0 and y=0 is prepared comprising preparing an aqueous solution comprising an Fe salt of one of the anions and an Fe salt of the other anion before bringing into contact with the composition of oil possessing surfactant properties.

8. The process as claimed in claim 1, wherein a material composed of nanoparticles of a compound

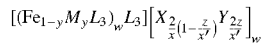

in which y≠0 and z≠0 is prepared comprising preparing a solution comprising at least one iron salt of one of the anions and at least one M salt of the other anion.

9. The process as claimed in claim 1, wherein a material composed of nanoparticles of a compound

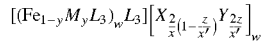

in which the nanoparticles are coated with silica is prepared comprising adding a silyl derivative to the reaction medium before step d).

10. The process as claimed in claim 9, wherein the silyl derivative is tetraethoxysilane, (n-octadecyl)triethoxysilane or (n-octyl)triethoxysilane.

11. A process for the direct preparation of a spin transition material composed of spherical nanometric particles comprising a compound corresponding to the formula:

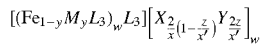

in which:
L represents a 1,2,4-triazole ligand carrying an R substituent on the nitrogen in the 4 position;
X is an anion having the valency x, 1≤x≤2;
Y is an anion other than X having the valency x', 1≤x'≤2;
R is an alkyl group or an $R^1R^2N$— group in which $R^1$ and $R^2$ represent, each independently of the other, H or an alkyl radical;
M is a metal having a $3d^4$, $3d^5$, $3d^6$ or $3d^7$ configuration, other than Fe;
0≤y≤1;
0≤z≤2;
3≤w≤1500;
the process comprising the following steps:
a) preparation of a microemulsion of a water-in-oil type by addition of an aqueous solution of at least one iron salt and optionally a precursor of the metal M to a solution of a surfactant in an oil and subjecting to ultrasound until a clear solution is obtained;
b) preparation of a microemulsion of a water-in-oil type by addition of an aqueous solution of ligand to a solution of a surfactant in an oil and subjecting to ultrasound until a clear solution is obtained;
c) mixing the two microemulsions and treating the mixture with ultrasound until a clear solution is obtained;
d) precipitation of the nanoparticles by addition of a solvent which does not modify the structure of the nanoparticles but which denatures the emulsion,
wherein the process does not comprise grounding of the spherical nanometric particles.

12. The process as claimed in claim 11, wherein R is an alkyl group having from 1 to 8 carbon atoms, or R is an $R^1R^2N$— group in which $R^1$ and $R^2$ represent, independently, H or an alkyl group having from 1 to 8 carbon atoms.

13. The process as claimed in claim 11, wherein each of the anions X and Y represents, independently, a monovalent anion selected from the group consisting of $BF_4^-$, $ClO_4^-$, $Br^-$, $Cl^-$ and $NO_3^-$ or a divalent anion selected from the group consisting of $SO_4^{2-}$ and $CO_3^{2-}$.

14. The process as claimed in claim 11, wherein M represents Zn, Mn, Ni or Co.

15. The process as claimed in claim 11, wherein a material composed of nanoparticles of a compound

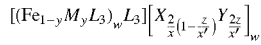

in which y≠0 and z=0 is prepared comprising preparing an aqueous solution of M salt and adding to the aqueous solution of Fe salt, before bringing into contact with the composition of oil possessing surfactant properties.

16. The process as claimed in claim 11, wherein a material composed of nanoparticles of a compound

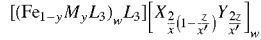

in which z≠0 and y=0 is prepared comprising preparing an aqueous solution comprising an Fe salt of one of the anions and an Fe salt of the other anion, before bringing into contact with the composition of oil possessing surfactant properties.

17. The process as claimed in claim 11, wherein a material composed of nanoparticles of a compound

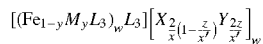

in which y≠0 and z≠0 is prepared comprising preparing a solution comprising at least one iron salt of one of the anions and at least one M salt of the other anion.

18. The process as claimed in claim 11, wherein a material composed of nanoparticles of a compound

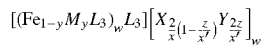

in which the nanoparticles are coated with silica is prepared comprising adding a silyl derivative to the reaction medium before step d).

* * * * *